(12) United States Patent
Leon

(10) Patent No.: US 10,383,763 B1
(45) Date of Patent: Aug. 20, 2019

(54) COOL FINGER SYSTEM

(71) Applicant: Marisela Leon, Watsonville, CA (US)

(72) Inventor: Marisela Leon, Watsonville, CA (US)

( * ) Notice: Subject to any disclaimer, the term of this patent is extended or adjusted under 35 U.S.C. 154(b) by 0 days.

(21) Appl. No.: 14/515,889

(22) Filed: Oct. 16, 2014

Related U.S. Application Data

(60) Provisional application No. 61/905,789, filed on Nov. 18, 2013.

(51) Int. Cl.
| | | |
|---|---|---|
| *A61F 7/00* | (2006.01) | |
| *A61F 7/02* | (2006.01) | |
| *A61F 5/10* | (2006.01) | |
| *A61F 5/058* | (2006.01) | |
| *A61F 13/10* | (2006.01) | |
| *A61F 7/10* | (2006.01) | |

(52) U.S. Cl.
CPC ............ *A61F 7/02* (2013.01); *A61F 5/05875* (2013.01); *A61F 5/10* (2013.01); *A61F 13/105* (2013.01); *A61F 7/10* (2013.01); *A61F 2007/0037* (2013.01); *A61F 2007/0038* (2013.01); *A61F 2007/108* (2013.01)

(58) Field of Classification Search
CPC .......... A61F 5/05875; A61F 5/10; A61F 7/00; A61F 7/02; A61F 2007/0001; A61F 2007/0037; A61F 2007/0038; A61F 2007/0219; A61F 2007/0231; A61F 2007/108

USPC ...................................... 602/2, 22; 2/21, 163
See application file for complete search history.

(56) References Cited

U.S. PATENT DOCUMENTS

| | | | |
|---|---|---|---|
| 4,668,564 A * | 5/1987 | Orchard .................... | A61F 7/02 264/46.4 |
| 5,111,810 A * | 5/1992 | Fortney ..................... | A61F 7/02 602/2 |
| 5,267,945 A | 12/1993 | Doctor et al. | |
| 6,478,761 B2 * | 11/2002 | Bracamonte-Sommer .................. | A61F 5/05866 602/22 |
| 7,794,486 B2 | 9/2010 | Quincy, III | |
| 8,002,721 B2 * | 8/2011 | Bretl ......................... | A61F 7/02 602/2 |
| 2006/0064046 A1 | 3/2006 | Kortuem et al. | |
| 2007/0239238 A1 * | 10/2007 | Nausid ................ | A61F 5/05866 607/96 |
| 2011/0054577 A1 | 3/2011 | Latham | |

* cited by examiner

*Primary Examiner* — Keri J Nelson

(57) ABSTRACT

A thermal digit wrap system includes a thermal digit wrap assembly having a first edge having at least one loop mated fastener strip, a second edge, a third edge having at least one hook mated fastener strap, a fourth edge; a top side; a bottom side; and an interior volume having at least one cooling gel located between the top side and the bottom side. The thermal digit wrap assembly is structured and arranged to enable it to act in a capacity of a splint and immobilizes an injured digit. The thermal digit wrap system provides an isolated cold-pack via cooling gel to reduce swelling and pain following an injury to the digit.

4 Claims, 5 Drawing Sheets

COOL FINGER SYSTEM

CROSS-REFERENCE TO RELATED APPLICATION

The present application is related to and claims priority from prior provisional application Ser. No. 61/905,789, filed Nov. 18, 2013 which application is incorporated herein by reference.

COPYRIGHT NOTICE

A portion of the disclosure of this patent document contains material which is subject to copyright protection. The copyright owner has no objection to the facsimile reproduction, by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art or material, to the presently described or claimed inventions, or that any publication or document that is specifically or implicitly referenced is prior art.

1. Field of the Invention

The present invention relates generally to the field of digit immobilizers and more specifically relates to a thermal digit wrap system.

2. Description of the Related Art

A digit is one of several most distal parts of a limb, such as fingers dr toes, present in many vertebrates. Humans normally have five digits on each extremity. Each digit is formed by several bones called phalanges, surrounded by soft tissue. Human fingers normally have a nail at the distal phalanx.

Each finger has an orderly somatotopic representation on the cerebral cortex in the somatosensory cortex area and a distributed, overlapping representation in the supplementary motor area and primary motor area. The somatosensory cortex representation of the hand is a dynamic reflection of the fingers on the external hand. We deal with our environment largely with our hands. One consequence of this, sooner or later familiar to every human being, is die occurrence of a broken, bruised, sprained, smashed, stubbed, scraped, cut, or burned finger or thumb. For such injuries, a cold-pack keeps the swelling down and relieves the pain, while a finger splint may be used to support and/or immobilize the digit to promote healing. Unfortunately, the cold gel-packs in the drugstore are too big, so that when you attempt to use one to relieve a hurt finger, you wind up half-freezing your entire hand which is not desirable.

Various attempts have been made to solve problems found in digit immobilizer art. Among these are found in: U.S. Pub. No. 2006/0064046 to Mamie A Kortuem et al; U.S. Pat. No. 7,794,486 to Roger Bradshaw Quincy, III; U.S. Pub. No. 2011/0054577 to Jeffrey W. Latham; and U.S. Pat. No. 5,267,945 to David Doctor et al. This prior art is representative of digit immobilizers. None of the above inventions and patents, taken either singly or in combination, is seen to describe the invention as claimed.

Ideally, a thermal digit wrap system would be user-friendly and safe in-use and, yet may operate reliably and be manufactured at a modest expense. Thus, a need exists for a thermal digit wrap system that provides an isolated cold-pack via a cooling gel to reduce swelling and pain following an injury to the digit and to avoid the above-mentioned problems.

BRIEF SUMMARY OF THE INVENTION

In view of the foregoing disadvantages inherent in the known digit immobilizer device art, the present invention provides a novel thermal digit wrap system (also referred to herein as 'Cool Finger System'). The general purpose of the present invention, which will Ire described subsequently in greater detail is to provide a thermal digit wrap system that includes an isolated cold-pack via a cooling gel to reduce swelling and pain following an injury to the digit, yet still maintain support as desired.

A thermal digit wrap system is disclosed herein comprising: a thermal digit wrap assembly having a first edge having at least one loop mated fastener strip, a second edge, a third edge having at least one hook mated fastener strip, a fourth edge; a top side; a bottom side; and an interior volume comprising at least one cooling gel located between the top side and the bottom side. The thermal digit wrap system comprises die thermal digit wrap assembly. The thermal digit wrap assembly is structured and arranged to enable it to act in a capacity of a splint and immobilize an injured digit. The thermal digit wrap system provides an isolated cold-pack via cooling gel to reduce swelling and pain following an injury to the digit.

The thermal finger splint assembly is reusable. The digit comprises for example an index finger of the user-wearer. The thermal finger wrap assembly is preferably rectangular in shape with the first edge and the third edge being longitudinal and parallel to one another, and the second edge and fourth edge being longitudinal and parallel to one another when in an assembled condition. The first edge, the second edge, the third edge, and the fourth edge are structured and arranged to define parameters of the top side and the bottom side and form the interior volume. The cooling gel housed in the thermal digit wrap system (interior volume) provides targeted relief and protection of broken, sprained, burned, and otherwise injured digit(s). The cooling gel comprises diethylene glycol. The cooling gel located in the interior volume may be stored in a freezer when in a non-use condition.

The hook mated fastener strap is wrapped around the digit, then adjustably-fastened preferably via the loop mated fastener strip to the hook mated fastener strap. The hook mated fastener strap and the loop mated fastener strip form a hook and loop fastener system when in an in-use condition with the thermal digit wrap system being removably-secured about the digit of a user-wearer. The thermal digit wrap assembly comprises exactly two hook mated fastener strap (s) in preferred embodiments with the two hook mated fastener strap(s) located on a top portion and a bottom portion of the third edge of the thermal digit wrap so its to provide more support and prevent movement of the digit when in the in-use condition.

A kit is also embodied herein for the thermal digit wrap system comprising at least: a plurality of thermal digit wrap assemblies sized to fit a thumb, an index finger, a middle finger, a ring finger, and a pinkie finger on the hand of tire user-wearer; and further comprising a set of user-instructions.

A method of use for a thermal digit wrap system is disclosed herein comprising the steps of: removing a digit-specific thermal digit wrap assembly from a freezer; placing the thermal digit wrap assembly around a digit that is injured; wrapping the thermal digit wrap assembly around the injured said digit; securing the thermal, digit wrap assembly around the injured digit via at least one hook and loop fastening system; allowing the thermal digit wrap assembly to reduce swelling and pain of the injured digit for approximately 10-15 minutes; unfastening the hook mated fastener strap; and removing the thermal digit wrap assembly for future use. The method may further comprise the step of placing the thermal digit wrap system in the freezer for future use.

The present invention holds significant improvements and serves as a thermal digit wrap system. For purposes of summarizing the invention, certain aspects, advantages, and novel features of the invention have been described herein, lit is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, thermal digit wrap system (Cool Finger System), constructed and operative according to the teachings of the present invention.

The various embodiments of the present invention will hereinafter be described in conjunction with the appended drawings, wherein like designations denote like elements

DETAILED DESCRIPTION

Figure 1:
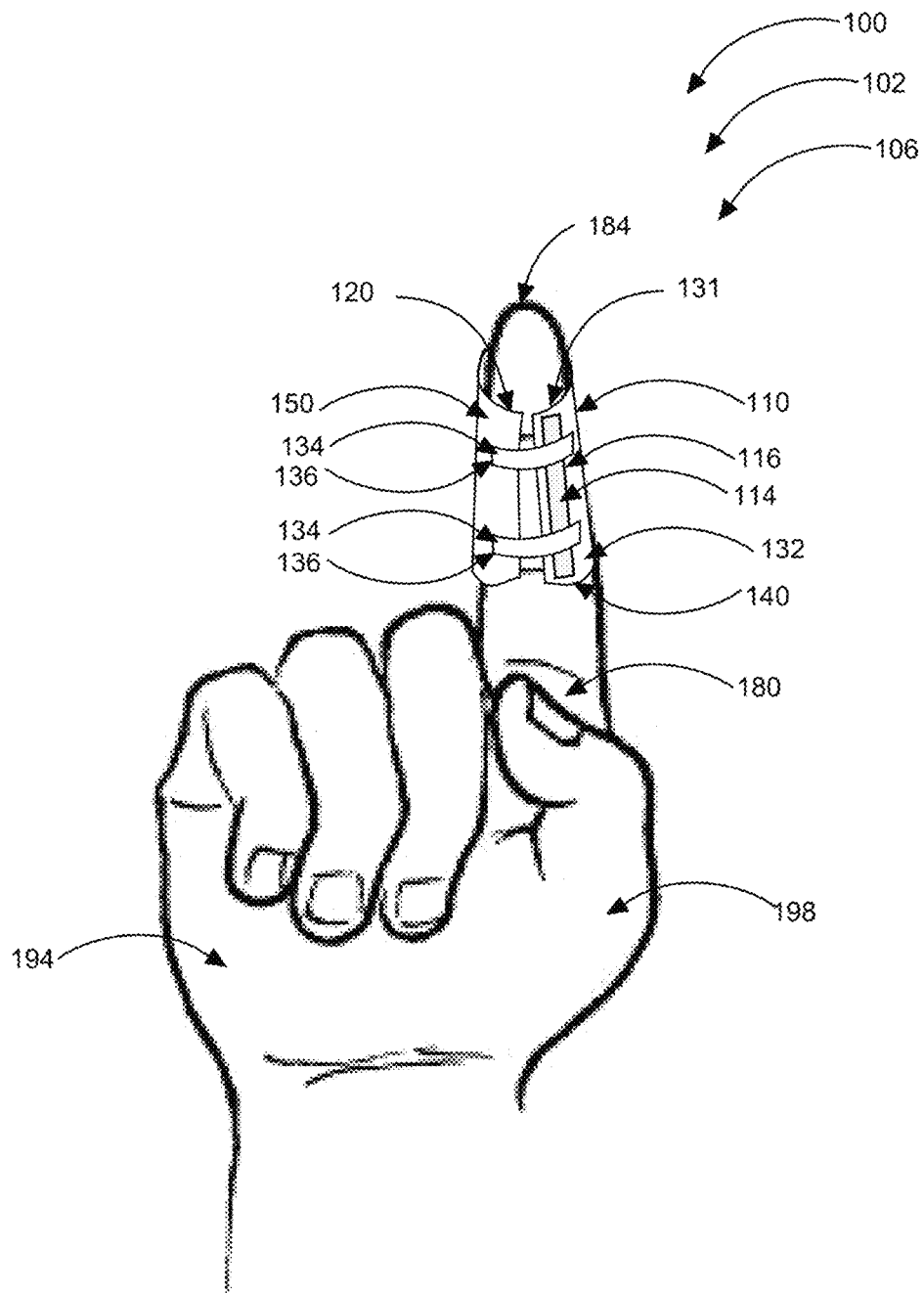
FIG. 1 shows a perspective view illustrating a thermal digit wrap system in an in-use condition according to an embodiment of the present invention.

As discussed above, embodiments of the present invention relate to a digit immobilizer device and more particularly to a thermal digit wrap system (Cool Finger System) to provide a thermal digit wrap system that includes an isolated cold-pack via a cooling gel to reduce swelling and pain following an injury to the digit.

Generally speaking the Cool Finger System comprises a specially designed product line of gel-filled cold-packs designed specifically for use with a hurt finger or thumb (digit). The Cool Finger System may be produced in Small, Medium, Large, and Extra-Large sizes, and may be suitable for use by individuals of both sexes and all ages. The Cool Finger System may be sold in a single-unit package or a multi-unit package; and the Cool Finger System may also be configured as either a re-usable or single-use disposable product. In either case (or both cases), the Cool Finger System may present itself as a rectangular gel-pack corresponding in length to the digit being fitted. The sides of the gel-pack may be equipped with four tabs such as VELCRO®, elastic; perhaps peel-n-stick adhesive-backed like BAND-AIDS®—designed to fasten across and around the finger being treated, and to hold the gel-pack securely and comfortably in place. This universal, easily adaptable design permits tire Cool Finger System to be placed and secured to either the top of the finger or thumb (dorsal surface) or to the underside (palmar surface).

The user may simply chill the Cool Finger System gel-pack sufficiently in the freezer, and then apply the device to tire injured finger or thumb, likely limiting the icing-down period to 10 or 15 minutes at a time, and re-chilling the Cool Finger System as needed. The Cool Finger System may thus function as a cold-pack to reduce swelling and pain following an injury to a finger or thumb; and also function in a limited capacity as a means of splinting, or immobilizing in an anatomically correct alignment a sprained and swollen finger or thumb.

The great advantage of the Cool Finger System is that it puts the cold where it counts, and where it is needed. Rather than subjecting one's entire hand to an icing-down, this Cool. Finger System may ice only that digit that had suffered injury. An essential item to have in one's home, office, or car first-aid kit, the Cool Finger System may be kept in storage indefinitely, then chilled and used whenever a thumb or finger mishap occurs. To be produced in a range of sizes appropriate for toddlers, children, adolescents, and adults, the Cool Finger System is unique in conception, thoughtful in design, conceived to meet a need, shared by millions of consumers.

Referring now to the drawings by numerals of reference there is shown in FIGS. 1-4, various views of thermal digit wrap assembly 102 of thermal digit wrap system 100 according to embodiments) of the present invention.

Thermal digit wrap system 100 in a preferred embodiment comprises: thermal digit wrap assembly 102 having first edge 110 having at least one loop mated fastener strip 114, second edge 120, third edge 130 having at least one hook mated fastener strap 134, fourth edge 140: top side 150; bottom side 160; and interior volume 170 comprising at least one cooling gel 174 located between top side 150 and bottom side 160. Thermal digit wrap system 100 preferably comprises thermal digit wrap assembly 102. Thermal digit wrap assembly 102 is structured and arranged to enable it to act in a capacity of a splint and immobilizes an injured digit 180. Thermal digit wrap system 100 provides an isolated cold-pack via cooling gel 174 to reduce swelling and pain following an injury to digit 180.

Thermal finger splint assembly 102 is reusable in a preferred embodiment Thermal finger splint assembly 102 may also be disposable is some embodiments and may include optional elastic for securing thermal finger splint assembly 102 around digit 180 of user-wearer 198 in lieu of loop mated fastener strip 114 and hook mated fastener strap 134 (not shown). Digit 180 may comprise thumb 182, index finger 184 as shown in FIG. 1 in in-use condition 106, middle finger 186, ring finger 188, or pinkie finger 190 on hand 194 of user-wearer 198 as shown in kit 400 in FIG. 4.

Figure 2:
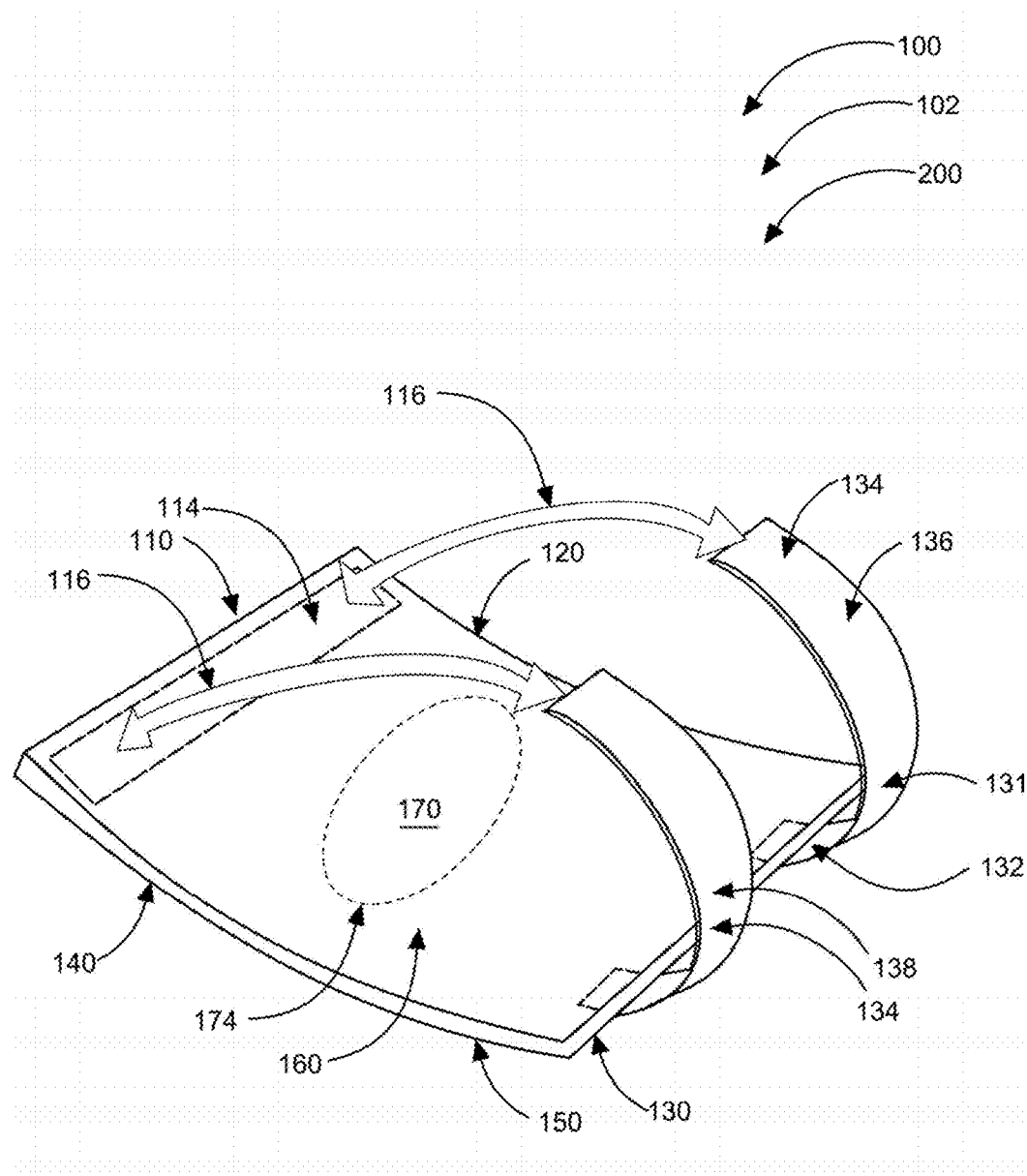
FIG. 2 is a front perspective view illustrating a thermal digit wrap assembly of the thermal digit wrap system according to an embodiment of the present invention of FIG. 1.
Figure 3:
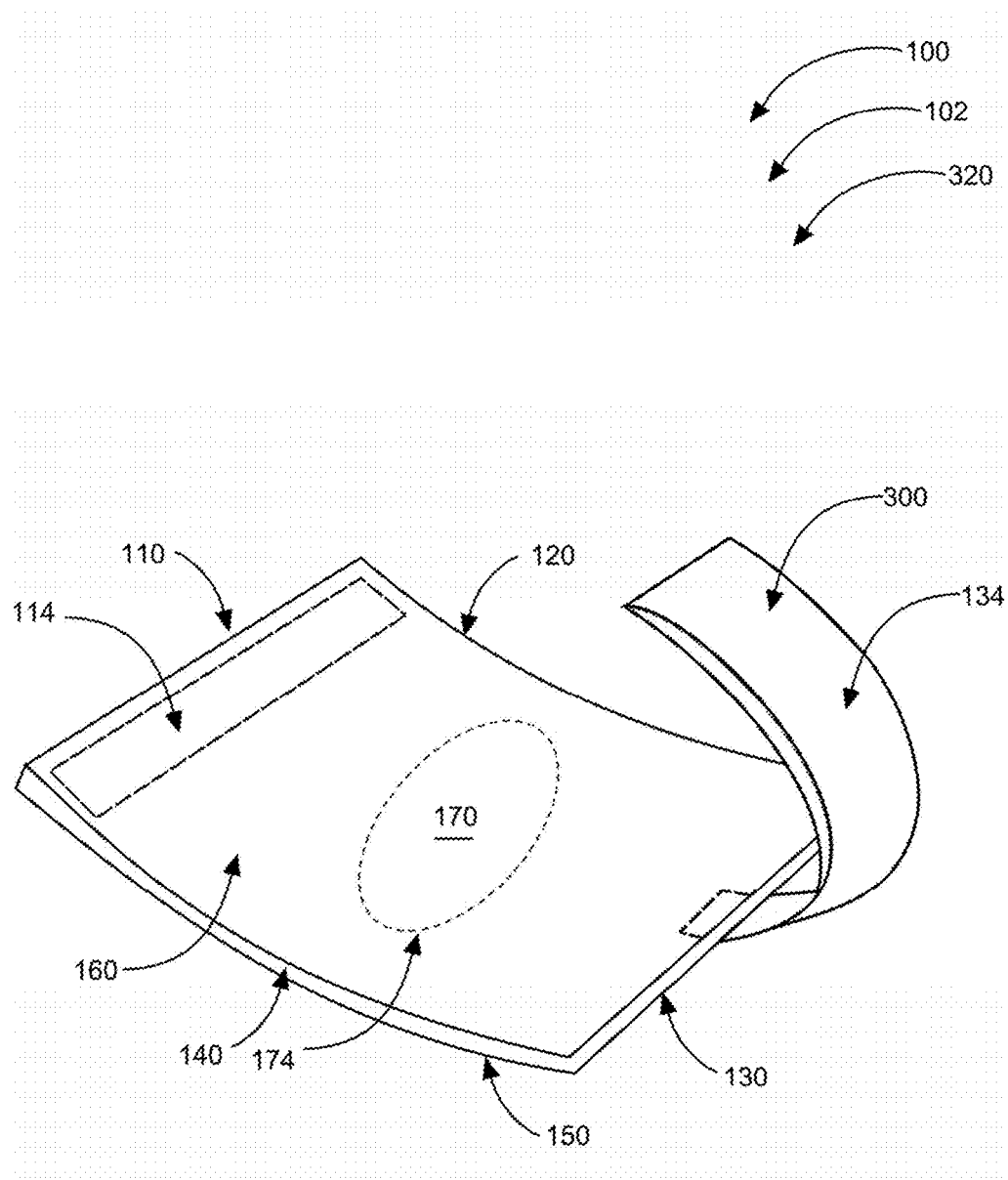
FIG. 3 is a front perspective view illustrating a thermal digit wrap assembly of tike thermal digit wrap system according to an embodiment of the present invention of FIG. 1.

Thermal finger wrap assembly 102 is preferably rectangular in shape with first edge 110 and third edge 130 being longitudinal and parallel to one another, and second edge 120 anti fourth edge 140 being longitudinal and parallel to one another when in assembled condition 200 as shown in FIGS. 2 and 3. First edge 110, second edge 120, third edge 130, and fourth edge 140 are structured and arranged to define parameters of top side 150 and bottom side 102 and form interior volume 170. Cooling gel 174 housed in thermal digit wrap system 100 (interior volume 170) provides targeted relief and protection of broken, sprained, burned, and otherwise injured digit(s) 180.

Cooling gel 174 located in interior volume 170 may be stored in a freezer when in a non-use condition. Further, cooling gel 174 located in interior volume 170 may be cooled in a refrigerator when in a non-use condition so as to store coolness for future use. Cooling gel 174 comprises diethylene glycol. Upon reading this specification, it should be appreciated that, under appropriate circumstances, considering such issues as user preferences, design preference, structural requirements, marketing preferences, cost, available materials, technological advances, etc., other cooling gel arrangements such as, for example, ethylene glycol, etc., may be sufficient.

Hook mated fastener strap(s) 134 is wrapped around digit 180, then adjustably-fastened via loop mated fastener strip 114 to book mated fastener strap 134. Other fastening means may be used. Hook mated fastener strap 134 and loop mated fastener strip 114 form hook and loop fastener system 116 when to in-use condition 106 with the thermal digit wrap system 100 being removably-secured about digit 180 of user-wearer 198 as shown in FIG. it. Thermal digit wrap assembly 102 in a preferred embodiment comprises exactly two said hook mated fastener strap(s) 134 (first hook mated fastener strap 136 and second book mated fastener strap 138) first hook mated fastener strap 136 and second hook mated fastener strap 138 located on top portion 131 and bottom portion 132 of third edge 130 of thermal digit wrap assembly 102 so as to provide more support and prevent movement of digit 180 when in in-use condition 106 as shown in FIGS. 1 & 2.

In an alternate embodiment thermal digit wrap assembly 106 comprises exactly one hook mated fastener strap 300, with exactly one hook mated fastener strap 300 located on center region 310 on third edge 130 of thermal digit wrap assembly 102 so as to provide less tension on digit 180 when in an alternate in-use condition 320 as shown in FIG. 3. Upon reading this specification, it should be appreciated that, under appropriate circumstances, considering such issues as user preferences, design preference, structural requirements, marketing preferences, cost, available materials, technological advances, etc., other fastener arrangements such as, for example, a pressure sensitive adhesive in disposable embodiments, elastic, etc., may be sufficient.

Figure 4:
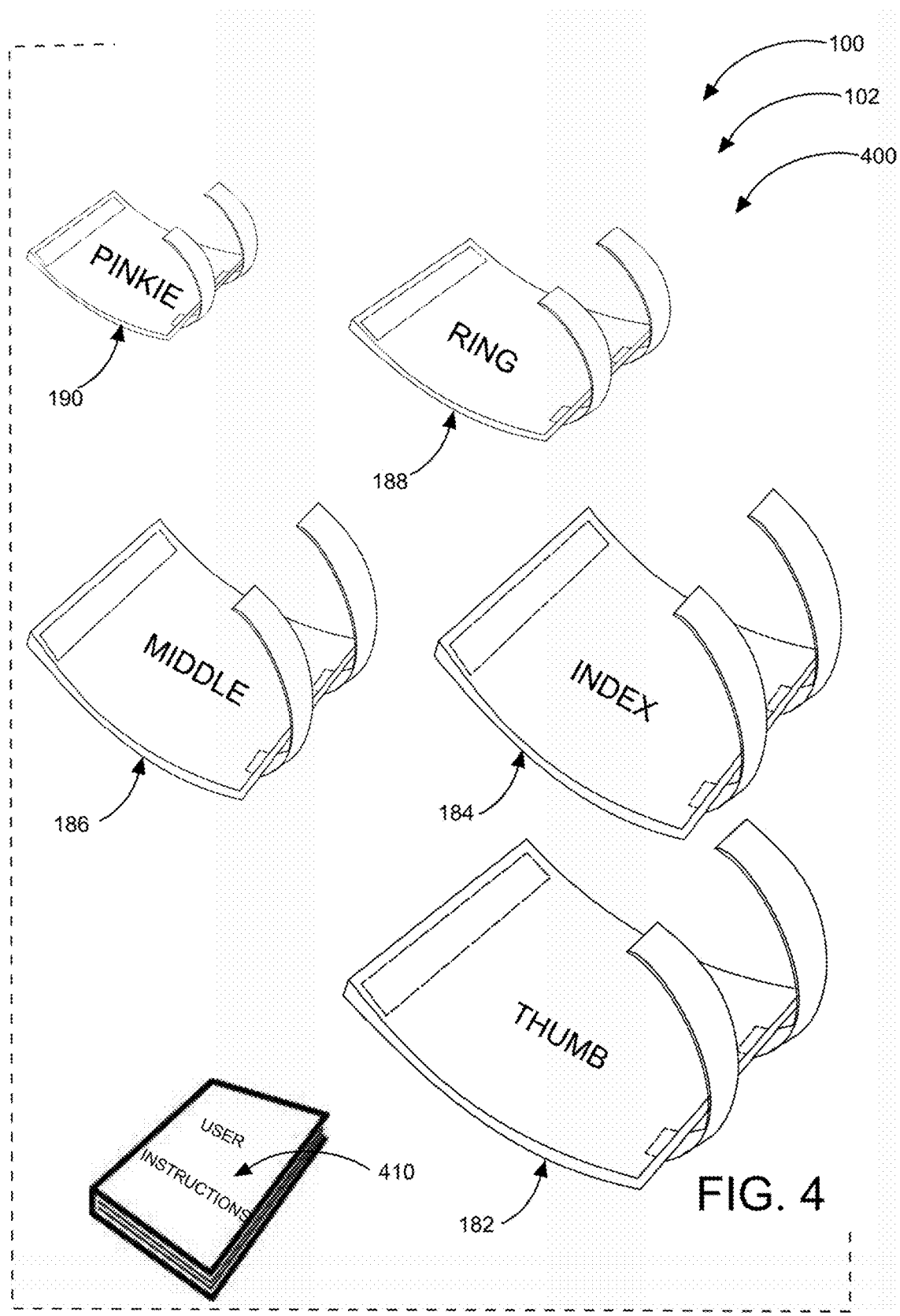
FIG. 4 is a perspective view illustrating a kit of the thermal digit wrap system according to an embodiment of the present invention of FIG. 1.

Referring now to FIG. 4 showing a perspective view illustrating a kit of the thermal digit wrap system according to an embodiment of the present invention of FIG. 1.

Thermal digit wrap system 100 may be sold as kit 400 comprising the following pans: a plurality of thermal digit wrap assemblies 102 sized to fit thumb 182, index finger 184, middle finger 186, ring finger 188, and pinkie finger 190 on hand 194 of user-wearer 198: and further comprising set of user-instructions 410. The kit has instructions such that functional relationships are detailed in relation to the structure of the invention (such that the invention can be used, maintained, or the like in a preferred manner). Thermal digit wrap system 100 may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different color combinations, parts may be sold separately, etc., may be sufficient.

Figure 5:
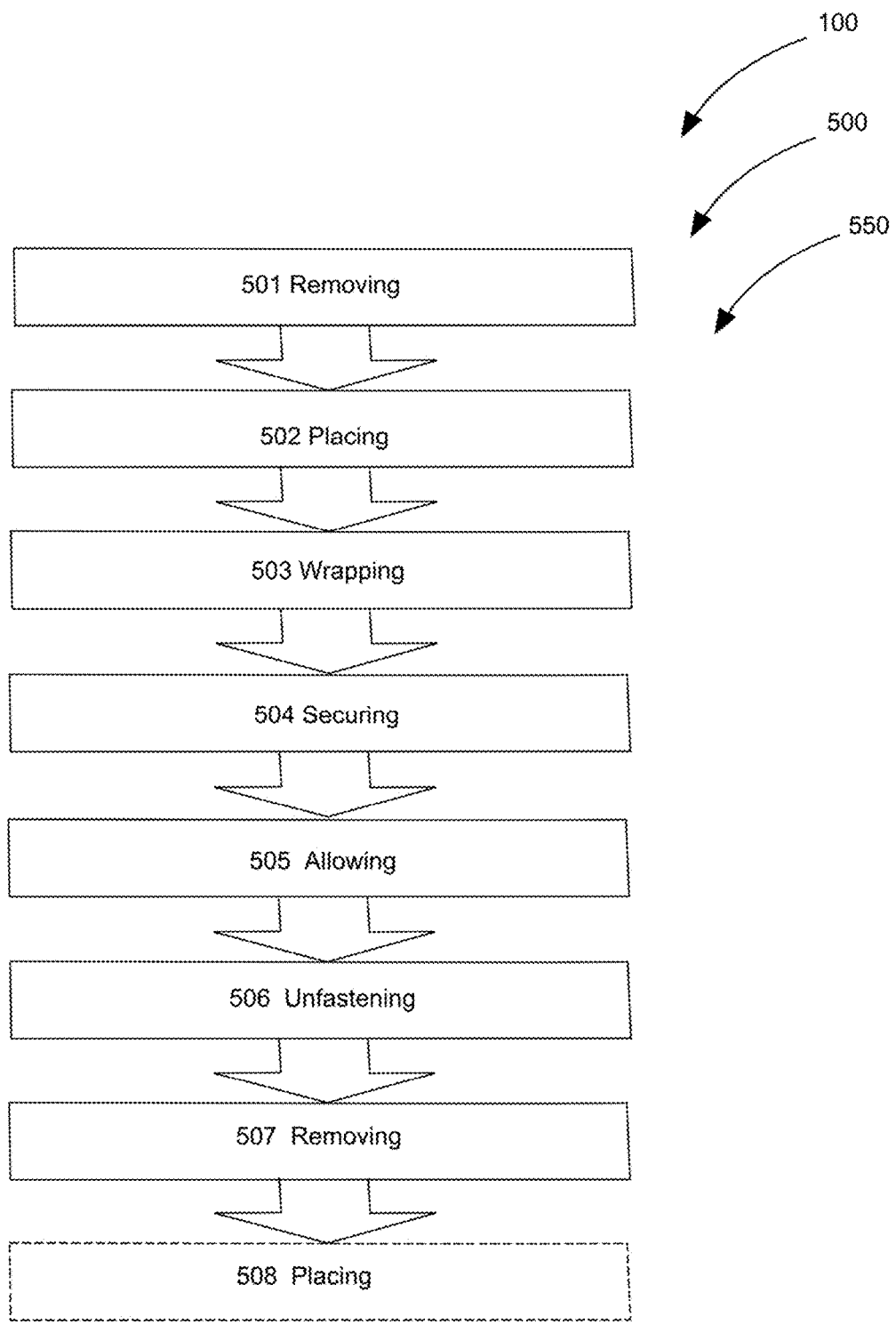
FIG. 5 is a flowchart illustrating a method of use for the thermal digit wrap system according to an embodiment of the present invention of FIGS. 1-4.

Referring now to FIG. 5, flowchart 550 illustrating method of use 500 for thermal digit wrap system 100 according to an embodiment of the present invention of FIGS. 1-4.

Method of use 500 of for thermal digit wrap system 100 preferably comprises the steps of step one 501 removing a digit-specific thermal digit wrap assembly 102 from a freezer; step two 502 placing thermal digit wrap assembly 102 around digit 180 that is injured; step three 503 wrapping thermal digit wrap assembly 102 around injured digit 180; step four 504 securing thermal digit wrap assembly 102 around injured digit 180 via at least, one hook and loop fastening system 116; step five 505 allowing thermal digit wrap assembly 102 to reduce swelling and pain of injured digit 180 for approximately 10-15 minutes; step six 506 unfastening hook mated fastener strap 134; and step seven 507 removing thermal digit wrap assembly 102 for future use. The method further comprising step eight 508 placing said thermal digit wrap system 100 in said freezer for future use.

It should be noted that step 507 is an optional step and may not be implemented, in all cases. Optional steps of method 500 are illustrated using dotted lines in FIG. 5 so as to distinguish them from the other steps of method 500.

It should be noted that the steps described in the method of use can be carried out in many different orders according to user preference. The use of "step of" should not be interpreted as "step for", in the claims herein and is not intended to invoke the provisions of 35 U.S.C. § 112.16. Upon reading this specification, it should lie appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding; certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A thermal digit wrap system comprising:
a thermal digit wrap assembly having,
   a first edge having one loop mated fastener strip having a longitudinal length extending substantially parallel along said first edge;
   a second edge;
   a third edge having two hook mated fastener straps each having a longitudinal length extending outwardly and substantially perpendicular from said third edge;
   a fourth edge;
   a top side;
   a bottom side; and
   an interior volume comprising at least one cooling gel located between said top side and said bottom side;
wherein said thermal digit wrap assembly is reusable;
wherein said thermal digit wrap assembly is rectangular in shape with said first edge and said third edge being longitudinal and parallel to one another, and said second edge and said fourth edge being longitudinal and parallel to one another;
wherein said first edge, said second edge, said third edge, and said fourth edge are structured and arranged to define parameters of said top side and said bottom side and form said interior volume;
wherein said hook mated fastener straps and said loop mated fastener strip form a hook and loop fastener system;
wherein said thermal digit wrap assembly is configured to be wrapped around a user's injured digit and adjustably secured in place by said hook and loop fastener system;
wherein said thermal digit wrap assembly is structured and arranged to enable it to act in a capacity of a splint and immobilizes said digit;
wherein said thermal digit wrap system provides an isolated cold-pack via said at least one cooling gel to reduce swelling and pain following an injury to said digit;
wherein said at least one cooling gel housed in said thermal digit wrap system provides targeted relief and protection of said digit; and
wherein said cooling gel comprises diethylene glycol.

2. The thermal digit wrap system of claim 1 further comprising a kit including: a plurality of said thermal digit wrap assemblies sized to fit a thumb, an index finger, a middle finger, a ring finger, and a pinkie finger on a hand of said user; and further comprising a set of user-instructions.

3. A method of using said thermal digit wrap system of claim 1 comprising the steps of:
removing said thermal digit wrap assembly from a freezer;
placing said thermal digit wrap assembly around said digit that is injured;
wrapping said thermal digit wrap assembly around said digit;
securing said thermal digit wrap assembly around said digit via said hook and loop fastener system;
allowing said thermal digit wrap assembly to reduce swelling and pain of said digit for approximately 10-15 minutes;
unfastening said hook and loop fastener system; and
removing said thermal digit wrap assembly for future use.

4. The method of claim 3 further comprising the step of placing said thermal digit wrap system in said freezer for future use.

* * * * *